United States Patent [19]

Effland et al.

[11] Patent Number: 5,051,430
[45] Date of Patent: Sep. 24, 1991

[54] 3-(1H-INDAZOL-3-Y1)-4-PYRIDINAMINES

[75] Inventors: Richard C. Effland; Joseph T. Klein, both of Bridgewater, N.J.

[73] Assignee: Hoechst-Roussel Pharmaceuticals Incorporated, Somerville, N.J.

[21] Appl. No.: 579,751

[22] Filed: Sep. 10, 1990

[51] Int. Cl.$^5$ .................. A61K 31/44; C07D 401/04
[52] U.S. Cl. .................................. 514/338; 514/352; 546/271; 546/309; 546/311
[58] Field of Search ................... 546/271; 514/338

[56] References Cited

PUBLICATIONS

WO 8808842A.
WO 8400007A.

Primary Examiner—Jane T. Fan
Attorney, Agent, or Firm—Elliott Korsen

[57] ABSTRACT

This invention relates to 3-(1H-indazol-3-yl)-4-pyridinamines of the formula

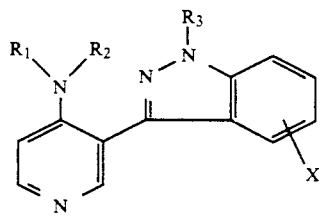

where $R_1$ is hydrogen, loweralkyl, arylalkyl or acyl; $R_2$ is hydrogen, loweralkyl or arylalkyl; $R_3$ is hydrogen, loweralkyl or aryl and X is hydrogen, halogen, nitro or amino or the pharmaceutically acceptable addition salts thereof, and where applicable, the geometric and optical isomers and racemic mixtures thereof. The compounds of this invention are useful as analgesics and as topical antiinflammatory agents for the treatment of various dermatoses.

9 Claims, No Drawings

3-(1H-INDAZOL-3-YL)-4-PYRIDINAMINES

This invention relates to 3-(1H-indazol-3-yl)-4-pyridinamines of the formula

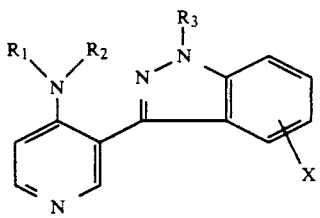

where $R_1$ is hydrogen, loweralkyl, arylalkyl or acyl; $R_2$ is hydrogen, loweralkyl or arylalkyl; $R_3$ is hydrogen, loweralkyl or aryl and X is hydrogen, halogen, nitro or amino, or the pharmaceutically acceptable addition salts thereof, and where applicable, the geometric and optical isomers and racemic mixtures thereof. The compounds of this invention are useful as analgesics and as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Also included within the scope of this invention are compounds of formula II where $R_1$, $R_2$ and X are as defined above, which are useful as analgesics and also as direct precursors of the compounds of formula I.

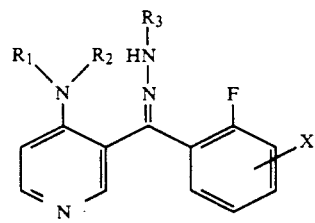

Throughout the specification and appended claims, a given chemical formula or name shall encompass all stereo, optical and geometrical isomers thereof and racemic mixtures thereof where such isomers and mixtures exist.

Unless otherwise stated or indicated, the following definitions shall apply throughout the specification and the appended claims.

The term "loweralkyl" refers to a straight or branched chain hydrocarbon of 1 to 6 carbon atoms, containing no unsaturation, e.g., methyl, ethyl, propyl, isopropyl, 2-butyl, neopentyl, n-hexyl, etc.; the term "arylalkyl" refers to a monovalent substituent which consists of a phenyl group, optionally substituted, as defined by the formula

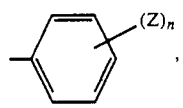

where Z is defined below, and n is an integer of 1 to 3, linked through an alkylene group having its free valence bond from a carbon of the alkylene group, having a formula of

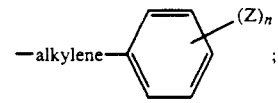

where Z is hydrogen, halogen, loweralkyl, loweralkoxy, trifluoromethyl, nitro and amino; the term alkylene refers to a bivalent radical of the lower branched or unbranched alkyl group it is derived from having valence bonds from two terminal carbons thereof, e.g., methylene ($-CH_2-$), ethylene ($-CH_2CH_2$)—, propylene ($-CH_2CH_2CH_2-$), isopropylene

etc.; the term "acyl" refers to a substituent having the formula

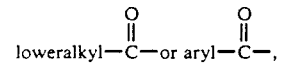

e.g., where aryl is an optionally substituted phenyl group as defined above, e.g. acetyl, formyl, benzoyl, etc., and the term "halogen" refers to a member of the halogen family consisting of fluorine, chlorine, bromine and iodine.

The compounds of this invention are prepared in the following manner. The substituents $R_1$, $R_2$ and $R_3$ are as defined above and X is hydrogen, halogen or nitro.

A hydrazone of the formula

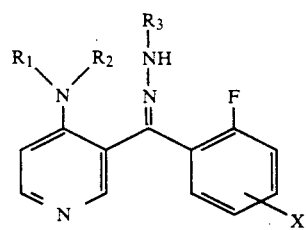

is cyclized in the presence of a base to afford Compound I. This reaction typically takes place in the presence of a strong base such as potassium carbonate, sodium carbonate, etc. in a suitable solvent such as dimethylformamide, at a temperature of about 0° to 160° C. for 1 to 24 hours.

Compound II is prepared by reacting a compound of the formula

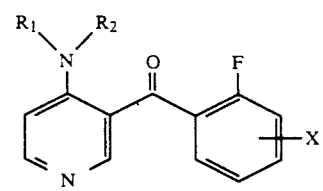

with a hydrazine. This reaction typically takes place in a loweralkanol solvent such as ethanol, butanol, etc. at a temperature of about 60°–120° C. for 1 to 24 hours.

The ketone starting material can be prepared in the following manner.

2,2-dimethyl-N-(4-pyridinyl)propanamide of the formula

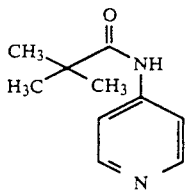

is allowed to react with n-butyllithium and the resultant dianion is allowed to react with ortho-fluorobenzaldehyde of the formula

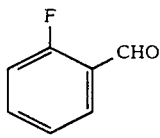

to afford compound IV of the formula

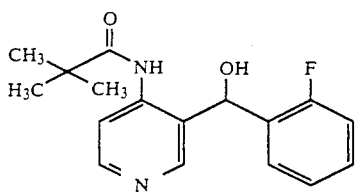

(IV)

Compound IV is oxidized to afford Compound IIIa of the formula

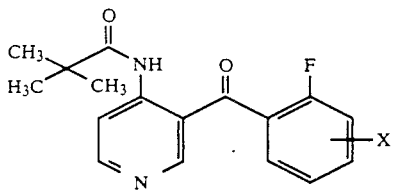

(IIIa)

This reaction is typically conducted with the aid of pyridinium dichromate and a suitable solvent such as dimethylformamide or halogenated hydrocarbon at a temperature of about 0° to 150° C. The propanamide is prepared as described in Turner, J.Org. Chem., 48, 3401–3408 (1983).

The compounds of the present invention are useful as analgesic agents. This utility is demonstrated in the phenyl-para-quinone writhing assay in mice, a standard assay for analgesia [Proc. Soc. Exptl. Biol. Med., 95, 729 (1957)]. The analgesic effect of compounds of the invention, expressed as % inhibition of writhing, is presented in Table 1.

TABLE 1

| Compound | Dose (mg/kg of body wt., s.c.) | % Inhibition of Writhing |
|---|---|---|
| [4-(2,2-dimethylpropionamido)-3-pyridinyl]-2-fluorophenyl-methanonehydrazone maleate | 20 | 60 |

TABLE 1-continued

| Compound | Dose (mg/kg of body wt., s.c.) | % Inhibition of Writhing |
|---|---|---|
| (4-Amino-3-pyridinyl)-2-fluorophenylmethanone hydrazone dihydrochloride | 20 | 74 |
| Propoxyphene (standard) | 3.9 | 50 |

The analgesic relief of pain is achieved when the compounds of the invention are administered to a subject requiring such treatment at an effective oral, parenteral or intraveneous dose of from 0.1 to 25 mg/kg of body weight per day, a particularly effective amount is about 5 mg/kg of body weight per day. It is to be understood that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The compounds of the present invention are also useful as topical antiinflammatory agents for the treatment of various dermatoses as described earlier.

The dermatological activity of the compounds of this invention was ascertained with reference to the following method.

TPA-INDUCED EAR EDEMA (TPAEE)

The purpose of this assay was to determine the ability of a topically-applied compound to prevent ear edema induced by topical application of TPA (phorbol 12-myristate acetate). Femals Swiss Webster mice topically received TPA (10 μg/ear) on the right ear and vehicle on the left ear. The test compound (10 μg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50}=47$ μg/ear). See Young, J.M. et al., J.Invest. Dermatol., 80 (1983), pp. 48–52.

Dermatological activity for some of the compounds of this invention are presented below in Table 2.

TABLE 2

| Compound | TPAEE (10 μg/ear) |
|---|---|
| N-[3-1H-Indazol-3-yl)-4-pyridinyl]-2,2-dimethyl-propanamide | −31% |

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel TM, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
3-(1-Methyl-1H-indazol-3-yl)-4-pyridinamine;
3-(1-Phenyl-1H-indazol-3-yl)-4-pyridinamine;
3-(1-Methyl-1H-indazol-3-yl)-N-methyl-4-pyridinamine;
3-(1-Methyl-1H-indazol-3-yl)-N-phenylmethyl-4-pyridinamine;
3-(5-Nitro-1H-indazol-3-yl)-4-pyridinamine;
3-(5-Amino-1H-indazol-3-yl)-4-pyridinamine; and
3-(6-Fluoro-1H-indazol-3-yl)-4-pyridinamine.

The following examples are given for illustrative purposes and are not to be construed as limiting the invention described herein.

EXAMPLE 1

[4-(2,2-Dimethylpropionamido)-3-pyridinyl]-2-fluorophenylmethanonehydrazone maleate A solution of [4-(2,2-dimethylpropionamido)-3-pyridinyl]-2-fluorophenylmethanone (9.8 g) and hydrazine monohydrate (3.3 g) in 100 mL ethanol was stirred at reflux for five hours, cooled, stirred with ice-water and extracted with ethyl acetate-ether. The dried organic layer was filtered and evaporated. The residue was eluted through silica with dichloromethane then 15% ethyl acetate in dichloromethane via flash column chromatography and then was triturated with hexane-ether to yield 7 g of [4-(2,2-dimethylpropionamido)-3-pyridinyl]-2-fluorophenylmethanone-hydrazone, as a solid, m.p. 78°-82° C. Four grams were converted to the maleate salt in methanol-ether and thereafter recrystallized from methanol-ether to yield 2.3 g of crystals, d 161°-162° C.

Analysis:
Calculated for $C_{21}H_{23}FN_4O_5$: 58.59% C; 5.39% H; 13.02% N.
Found: 58.17% C; 5.35% H; 12.93% N.

EXAMPLE 2

(4-Amino-3-pyridinyl)-2-fluorophenylmethanone hydrazone dihydrochloride

A solution of [4-(2,2-dimethylpropionamido)-3-pyridinyl]-2-fluorophenylmethanone hydrazone (6 g) in 60 mL methanol and 25 mL 20% aqueous sodium hydroxide was stirred at reflux for four hours, cooled, stirred with water and extracted with ethyl acetate. The organic extract was washed with water and dried. After filtration the solvent was removed to yield 4.5 g of an oil. This oil was eluted through silica with 10% methanol in dichloromethane via flash column chromatography to yield 3.5 g of an oil. This oil was converted to the dihydrochloride salt in methanol and evaporated. The residue was crystallized from methanol-ether to yield 2.4 g of crystals d 201°-203° C. This solid was recrystallized from 10% methanol in acetonitrile to yield 2.1 g of (4-amino-3-pyridinyl)-2-fluorophenylmethanone hydrazone dihydrochloride, 202°-203° C. (dec.).

Analysis:
Calculated for $C_{12}H_{13}Cl_2FN_4$: 47.54% C; 4.32% H; 18.48% N.
Found: 47.78% C; 4.32% H; 18.60% N.

EXAMPLE 3

N-[3-(1H-Indazol-3-yl)-4-pyridinyl]-2,2-dimethylpropanamide

A solution of [4-(2,2-dimethylpropionamido)-3-pyridinyl]-2-fluorophenymethanone hydrazone (7 g) in 60 mL dimethylformamide containing milled potassium carbonate (8 g) was warmed to 145°-150° C. After three hours the mixture was cooled, stirred with water and extracted with ethyl acetate. The dried (anhydrous magnesium sulfate) organic layer was filtered and evaporated to 7.5 g of an oil. The oil was combined with 3.5 g product obtained from a previous run and eluted through silica with 20% ethyl acetate in dichloromethane via flash column chromatography to yield 2.6 g of a solid, mp 218°–220° C. This solid was recrystallized from acetonitrile to yield 2.2 g of N-[3-(1H-Indazol-3-yl)-4-pyridinyl]-2,2-dimethylpropanamide, mp 232°–233° C.

Analysis:
Calculated for $C_{17}H_{18}N_4O$: 69.36% C; 6.16% H; 19.04% N.
Found: 69.45% C; 6.12 % H; 19.10% N.

EXAMPLE 4

3-(1H-Indazol-3-yl)-4-pyridinamine

A solution of N-[3-(1H-indazol-3-yl)-4-pyridinyl]-2,2-dimethylpropanamide (3.6 g) in 70 mL ethanol and 70 mL 20% aqueous sodium hydroxide was stirred at reflux for six hours then was cooled, stirred with water and extracted with ethyl acetate. The organic layer was washed with water and saturated sodium chloride then was dried (anhydrous magnesium sulfate), filtered and evaporated to yield 3 g of a solid. This solid was eluted through silica with 10% methanol in dichloromethane via flash column chromatography to yield 2.2 g of a solid, m.p. 234°–236° C. This solid was recrystallized from methanol to yield 1.7 g of 3-(1H-indazol-3-yl)-4-pyridinamine, m.p. 237°–239° C.

Analysis:
Calculated for $C_{12}H_{10}N_4$: 68.55% C; 4.79% H; 26.66% N.
Found: 68.32% C; 4.90% H; 26.47% N.

We claim:

1. A compound of the formula

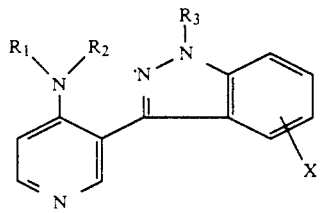

where $R_1$ is hydrogen, loweralkyl, arylalkyl or acyl; $R_2$ is hydrogen, loweralkyl or arylalkyl; $R_3$ is hydrogen, loweralkyl or aryl; X is hydrogen, nitro or amino, the term aryl in each occurrence signifying a phenyl group optionally substituted as defined by the formula

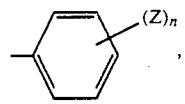

where Z is hydrogen, halogen, loweralkyl, loweralkoxy, trifluoromethyl, nitro and amino, and n is an integer of 1 to 3; the term acyl in each occurrence signifying a substituent having the formula loweralkyl

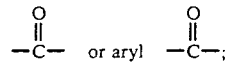

or a pharmaceutically acceptable addition salt thereof, or where applicable a geometrical or optical isomer or racemic mixture thereof.

2. The compound as defined in claim 1 wherein $R_1$ is acyl.

3. The compound as defined in claim 2 which is N-[3-(1H-indazol-3-yl)-4-pyridinyl]-2,2-dimethylpropanamide.

4. The compound as defined in claim 1 wherein $R_1$ and $R_2$ are hydrogen.

5. The compound as defined in claim 4 which is 3-(1H-indazol-3-yl)-4-pyridinamine.

6. An analgesic composition which comprises a pain alleviating effective amount of a compound as defined in claim 1 and a pharmaceutically acceptable carrier therefor.

7. A dermatological composition which comprises a compound as defined in claim 1 present in an amount effective for treating a skin disorder and a pharmaceutically acceptable carrier therefor.

8. A method of treating a patient in need of relief from pain which comprises administering to a mammal a pain alleviating effective amount of a compound as defined in claim 1.

9. A method of treating a patient in need of relief from a skin disorder which comprises administering to such a patient an effective amount of a compound as defined in claim 1.

* * * * *